United States Patent
Joshi

(10) Patent No.: US 8,389,020 B1
(45) Date of Patent: Mar. 5, 2013

(54) IMMEDIATE ACTION AND LONG-LASTING FORMULATION TO CONTROL MOSS AND LIVERWORT

(75) Inventor: Hemant N. Joshi, Parsippany, NJ (US)

(73) Assignees: Hemant N. Joshi, Parsippany, NJ (US); Tara Innovations LLC, Parsippany, NJ (US)

( * ) Notice: Subject to any disclaimer, the term of this patent is extended or adjusted under 35 U.S.C. 154(b) by 0 days.

(21) Appl. No.: 13/251,264

(22) Filed: Oct. 2, 2011

(51) Int. Cl.
*A61K 33/26* (2006.01)

(52) U.S. Cl. ............... 424/648; 504/116.1; 504/119; 504/120

(58) Field of Classification Search ............ 424/648
See application file for complete search history.

(56) References Cited

U.S. PATENT DOCUMENTS

| | | | | |
|---|---|---|---|---|
| 4,119,537 A | * | 10/1978 | Finkelstein | 210/764 |
| 4,936,898 A | * | 6/1990 | Nielsen | 504/120 |
| 7,396,801 B1 | * | 7/2008 | Livingston | 504/121 |

* cited by examiner

*Primary Examiner* — James H Alstrum Acevedo
*Assistant Examiner* — Monica Shin

(57) ABSTRACT

Ferrous sulfate and ferrous ammonium sulfate are known to kill moss and liverwort. They impart acidity in the lawn. Moss grows better in an acidic pH. The current invention proposes a formulation of ferrous sulfate or ferrous ammonium sulfate and zero valent iron with lime. Lime neutralizes the acidity produced by the ferrous salt and keeps the pH of the soil at 7 to 7.5. The formulation produces an immediate effect to eradicate moss and also provides a sustained effect over a long period. Another embodiment contains an addition of antimicrobial agents such as benzalkonium chloride, dichlorophen, and didecyldimethyl ammonium chloride to the ferrous sulfate-lime formulation.

6 Claims, No Drawings

IMMEDIATE ACTION AND LONG-LASTING FORMULATION TO CONTROL MOSS AND LIVERWORT

FIELD OF INVENTION

The present invention relates to a formulation of ferrous sulfate and zero valent iron with dual release rates to control moss and liverworts growth in lawns, patio, driveway, rooftops, golf courses, and on trees for an extended period.

BACKGROUND OF INVENTION

Mosses and liverworts are small, soft plants which grow like a mat in damp and shady locations. Both have similar life cycle and reproductive organs and they lack vascular system present in developed plants. Botanically, mosses are bryophytes or non-vascular plants. Mosses are haploid, i.e., they have single set of chromosomes. Family Bryophyta includes liverworts and hornworts.

The term moss in this text encompasses all the bryophytes.

Mosses have two phases in their life-cycle. In the first phase, spores germinate to form stem, leafs and rhizoid. This upon maturity produces a zygote (fertilized egg). Zygote does not form another moss, but a slender stock with a capsule at the top. This capsule contains spores which are released to produce more moss plants.

Fossil records date the appearance of moss 350 million years ago. Mosses can become a nuisance in the lawn, plant pots, plant beds, golf courses, on driveways, on roofs etc. Mosses can grow in extreme conditions and can sustain even sub-zero temperatures. Infestation with moss may stunt the growth of other plants, increases weeding cost; may kill the grass in the lawn, and may damage roof and walls.

Many fungicides, herbicides, and inorganic salts have been used to control and/or kill moss. The commonly used inorganic salts include ammonium sulfate, ferrous sulfate, ferrous ammonium sulfate, copper sulfate etc. U.S. Pat. No. 3,964,893 cited the preparation of ferric ammonium sulfate-ammonium sulfate double salt and showed that the double salt was as effective as ferrous sulfate to control moss and its greening effect. U.S. Pat. No. 4,202,858 showed the effectiveness of copper pipe in the water container to control moss. U.S. Pat. No. 4,276,732 described a bimetallic device of copper and lead to be placed on the rooftop. With the rain water, ions of metals were released and were shown to control moss. U.S. Pat. No. 4,605,550 described a method to prepare a delayed release formulation of ferrous sulfate to kill moss. The system contained a water soluble extender, a resin and a water-insoluble extender. U.S. Pat. No. 4,936,898 claimed the preparation of powder containing atomized copper and zinc with silica clay which was shown to have moss-killing effect. In the U.S. Pat. No. 5,108,481, ferrous sulfate powder was mixed with ammonium sulfate solution and pellets were formed in a pelletizer. U.S. Pat. No. 7,368,121 described a process of controlling moss by the application of sodium percarbonate. In another embodiment, lime was added to the product to control pH of the moss and thereby constrained development of additional moss. The pH value of 3% sodium percarbonate solution is 10 to 11. The U.S. Pat. No. 7,396,801 disclosed a formulation composition containing a source of nitrogen, a non-ionic surfactant, a metal containing salt and an acidic pH adjusting agent (pH 2.5 to 5). The metal containing salt was chosen from a group consisting of copper sulfate, zinc sulfate, iron sulfate and iron chloride.

The terms—"burning moss", "killing moss", "eradicating moss" and "controlling moss" have been used interchangeably in this patent application and they project the same meaning.

Moss prefers to grow in an acidic soil with pH between 5.0 and 5.5. Most plants grow well in the pH range 5.8 to 7.0. Ferrous sulfate when added to water produces acidic pH (pH 1.5 to 2.2) whereas lime in water produces alkaline pH (pH 12). But, spreading lime in the lawn produces a micro-environmental pH of about 7. Lime or quicklime is calcium oxide prepared from the thermal decomposition of limestone (calcium carbonate). There are mainly two types—high calcium quicklime and dolomitic quicklime. There are hydrated forms of each. High calcium quicklime contains 0 to 5% magnesium carbonate. Dolomitic quicklime contains 35 to 46% magnesium carbonate. Calcium quicklime can absorb water to produce hydrated lime which contains 72 to 74% calcium oxide and 23 to 24% water. Under normal atmospheric conditions, only calcium oxide hydrate producing a final composition of 46 to 48% calcium oxide, 33 to 34 percent of magnesium oxide and 15 to 17 percent of water. It is termed as dolomitic hydrated lime.

In this patent application, the term "Lime" refers to calcium oxide and any of these varieties described above.

Ferrous sulfate is inexpensive, easy to use, easily available and non-toxic to the environment. It is available in different hydrate forms. These are —$FeSO_4 \cdot H_2O$ (szomolnokite, relatively rare), $FeSO_4 \cdot 4H_2O$ (rozenite, relatively common), $FeSO_4 \cdot 5H_2O$ (siderotil, relatively rare), $FeSO_4 \cdot 6H_2O$ (ferrohexahydrite, relatively rare), and $FeSO_4 \cdot 7H_2O$ (melanterite, relatively common). Ferrous sulfate septahydrate ($FeSO_4 \cdot 7H_2O$) was used in the experiments.

In this patent, "ferrous sulfate" reflects any of these hydrates of ferrous sulfate. The term "ferrous salt" refers to ferrous sulfate and ferrous ammonium sulfate.

Ferrous sulfate is soluble in water and there is a high probability of it getting washed away during watering of plants or rain. Ferrous sulfate has an immediate detrimental effect on moss, but if it is washed away, moss can grow back after some time. It is therefore essential to provide a steady supply of an active compound over a long period preventing further growth of moss.

SUMMARY OF INVENTION

In this invention, the main objective was to prepare a formulation to control moss and liverworts, which has an immediate and sustained/long-lasting effect. For the purpose of this patent application, the sustained/long-lasting effect is defined as up to 2 years after the treatment.

It is an additional objective of this invention to provide a moss-controlling composition that will not be harmful to plants, animals, and human beings.

The inventor accomplished this and other objectives with a novel composition which could be sprayed over the moss. The present invention is a powder comprising of three key components: (1) ferrous sulfate, (2) lime and (3) zero valent iron (ZVI). Ferrous sulfate produces acidic pH in the microenvironment when spread over the moss. A slight acidic pH actually helps the growth of moss. Lime, being basic in nature, acts as a neutralizer and brings up the micro-environmental pH to about 7 to 7.5. An appropriate proportion of ferrous sulfate and lime produces a suitable micro-environmental pH which helps to kill the moss. ZVI is a fine iron powder which is not soluble in water. However, it reacts slowly with water containing dissolved oxygen to produce water-soluble salts $Fe(OH)_2$ and $Fe(OH)_3$. These salts do not have high water solubility compared to $FeSO_4$, but it is certainly much higher than ZVI.

Another objective of the invention is to prepare a formulation of ferrous sulfate, ZVI, and lime with a known antimicrobial agent effective against moss. The agent can be selected from a group consisting of benzalkonium chloride, dichlorophen, and didecyldimethyl ammonium chloride (DDDAC).

In another embodiment of the invention, the moss controlling formulation also contains ferrous ammonium sulfate instead of ferrous sulfate or in combination with ferrous sulfate.

In other embodiments of the invention, the moss controlling formulation also contains a fragrance or the combination of fragrances (0 to 10% w/w). The fragrances can be selected from a group consisting of jasmine, rose, lavender, vanilla, marigold, lily, petunia and gardenia.

In other embodiments of the invention, the moss controlling formulation may also contain a green or a brown color (0 to 5% w/w).

The amount of ferrous sulfate in the formulation ranged from 5 to 60%, w/w.

The amount of antimicrobial agent in the formulation, including benzalkonium chloride, dichlorophen, and DDDAC, ranged from 0 to 100 g per kilogram of formulation (0 to 10% w/w).

The amount of ZVI in the formulations ranged from 0 to 60%, w/w.

The amount of Lime in the formulations ranged from 20 to 80%, w/w.

This formulation can also have other applications. Ferrous sulfate is also useful to prevent depletion of phosphorous from pasture, turf-grass and filter strips. This formulation can be used with manure application on pasture, turf-grass and filter strips to reduce the initial loss of phosphate to the environment.

DETAILED DESCRIPTION

Ferrous sulfate and ferrous ammonium sulfate (Mohr's salt) are known to kill moss and have been used as a solution (for example, 3 ounces of salt in 5 gallons of water). Ferrous sulfate solution in water is acidic with pH values as low as 1 to 2. There are references which claim that moss grows better in a slight acidic pH. It is therefore important to add Lime to the formulation so that a neutral microenvironmental pH is obtained upon application of this formula. This pH is not suitable for the growth of moss. The exact mechanism of action for ferrous sulfate on moss growth is unknown. It is claimed to make the moss weak, and eventually it burns or kills it. Chemically, it is a reducing agent. However, the moss reappears after few days or months after ferrous sulfate application. It is possible that being water soluble, ferrous sulfate gets washed off. Thus, application of ferrous sulfate could be a temporary solution to get rid of moss.

Following are the factors which negatively affect the quality of lawn allowing moss to take over: too much wet soil, lack of nutrition, acidic pH, shade, compact soil, drought (lack of water makes the grass weak), and sandy soil (it drains out water too quickly and weakens the grass). One should water the lawn well, but must take care not to make it too wet or too dry. If the pH of the soil is too acidic, one should apply lime in autumn. If the soil is too compact, one needs to aerate it routinely. If the soil is sandy, it is important to add top soil to improve the quality. Application of fertilizer to the lawn helps it grow healthy and helps it to win the battle with moss. We need to rake the dead moss, apply grass seeds with fertilizers and also, the moss killer. With this, the area will be covered by new grass and the moss will not reappear. If necessary, give a second treatment of the moss killer to completely burn the moss out. However, sometimes moss is very hard to eradicate with natural means. In such cases, harsher treatment—such as an application of ferrous sulfate need to adopted. A good schedule is to apply ferrous sulfate or similar moss killer in spring.

The invention will now be described with the help of following examples. These examples have been provided to illustrate preferred embodiments of the invention but these are not meant to be limiting, in any way, the scope of this invention.

EXPERIMENT 1

In order to establish the effective concentration of ferrous sulfate in the formulation, mixtures of ferrous sulfate and lime with a ferrous sulfate concentration between 0 to 60% (w/w) were prepared (Table I) and applied to 6"×6" area in triplicate. Water was sprayed over the area. The day time high temperature was 40° F. during the experiment and the night temperature decreased to 28° F. In one day, area with 30% or more ferrous sulfate concentration treatment turned black burning all the moss (Table II). The areas with 10% and 20% moss treatment were black in a week. There was no effect of 100% lime on the moss. Thus, a minimum concentration of 10% is suitable for the satisfactory results within a week. When % ferrous sulfate was more than 30%, the moss turned black in one day.

TABLE I

Formulations of Ferrous sulfate and Lime prepared for testing against moss

| Sample # | % Lime | % Ferrous sulfate |
|---|---|---|
| 1 | 100 | 0 |
| 2 | 80 | 20 |
| 3 | 60 | 40 |
| 4 | 50 | 50 |
| 5 | 90 | 10 |
| 6 | 70 | 30 |
| 7 | 40 | 60 |

TABLE II

Effect of ferrous sulfate concentration on survival of moss. Blackened moss was as indication of dead moss.

| Formulation # | % Ferrous Sulfate | Day 1 | Day 2 |
|---|---|---|---|
| 1 | 0 | Green | Dark Green |
| 2 | 20 | Slight Green/Black | Black Green |
| 3 | 40 | Black | Black |
| 4 | 50 | Black | Black |
| 5 | 10 | Slight green/Black | Black Green |
| 6 | 30 | Black | Black |
| 7 | 60 | Black | Black |

EXPERIMENT II

In another experiment, 25 grams of ferrous sulfate was mixed with 75 grams of lime. The powder was spread over 100 sq.ft. area where moss was growing. Pure lime (100 g) and pure ferrous sulfate (25 g) were used as controls and were spread over separate areas where moss was growing. The effectiveness of 25% ferrous sulfate plus 75% Lime formulation was similar to 25 g of ferrous sulfate. Lime acted as a good diluent helping to spread ferrous sulfate more evenly. Only lime treatment did not have any effect on the moss.

EXPERIMENT III

In this experiment, a formulation with two release rates was prepared. Table III lists the compositions of three formulations containing different amounts of ferrous sulfate, ZVI and lime. Formulation 11 contained 25% ferrous sulfate whereas formulation #13 contained no ferrous sulfate. Formulation 11 contained no zero valent iron.

TABLE III

Formulations containing different percentages of ferrous sulfate and zero valent iron.

| Ingredient | Formula #11 | Formula #12 | Formula #13 |
|---|---|---|---|
| Ferrous sulfate | 25 | 15 | 0 |
| Zero Valent Iron (ZVI) | 0 | 10 | 25 |
| Lime | 75 | 75 | 75 |

Each formulation, 50 g, was applied over about 250 to 300 sq.ft area where moss was growing in the month of May. Table IV shows the effects of each treatment on moss eradication. Formulation #11 contained 25% ferrous sulfate and it killed the moss in one day. Formulation #12 had lower concentration of ferrous sulfate (15%) and it had slower effect. Formulation #13 had no effect in eradicating moss in the beginning and 70 to 80% moss was killed in 24 days. After 15 months, all the three patches did not show revival of moss suggesting effectiveness over an extended period. These patches were next to each other and it is possible that ZVI got spread over all the areas with time and mainly over the area, which received the treatment from Formulation #11. The results clearly indicated the fast action of ferrous sulfate and slow/sustained action by ZVI. In a preliminary experiment a pinch of ZVI powder was spread over 35 inch$^2$ area covered with moss and the moss got eradicated with time. It showed the effect of ZVI to eradicate moss.

A sample of ZVI was obtained from Hepure Technologies. ZVI has several other applications including soil and ground water remediation. In the formulations, one can also use generic granular iron metal powder. Iron metal powder is highly reactive and may contain contaminants such as carbon, silicon, manganese, and phosphorous.

For the purpose of this patent, the term "ZVI" encompasses the product from Hepure Technologies as well as iron metal powder of particle size from 10 micron to 3 mm and with varying percentage of contaminants such as carbon, silicon, manganese, phosphorous etc. The sustained effect of iron metal particles depends upon the particle size of iron metal—larger the particles, longer the effect.

TABLE IV

Controlled release effect of zero valent iron (ZVI) on the survival of moss.

| Time | Formulation #11 | Formulation #12 | Formulation #13 |
|---|---|---|---|
| 1 day | Dark Black | Light Black | Green |
| 5 days | Dark Black | Light Black | Green with few black spots |
| 8 days | Dark Black | Light Black | Green with light black |
| 24 days | Dark Black | Light Black | 70% to 80% portion black with few green patches |
| 15 months | Dark Black | Dark Black | Dark Black |

EXPERIMENT IV

There are several solution formulations containing benzalkonium chloride, dichlorphen or DDDAC used to eradicate moss. Overall, 250 grams of these active are spread over 1000 sq. ft. in a solution form. Because these are very effective bactericidal, fungicidal and algaecidal molecules, they have a different mechanism of action than ferrous sulfate. Combination of ferrous sulfate with one of these agents is more effective. In the following example, the molecules are delivered in a powder form instead of a solution. The actives once spread over lawn dissolve upon watering and it is available in high concentration in the micro-environment of the lawn.

The following example the method of preparation of such a formulation with formula described in Table V. It contained 25% ferrous sulfate and 2% benzalkonium chloride as actives. Benzalkonium chloride is highly water soluble.

TABLE V

Anti-moss formulation composition with ferrous sulfate and an antibacterial agent.

| Ingredient | Percent, w/w |
|---|---|
| Ferrous sulfate | 25 |
| Benzalkonium chloride | 2 |
| Lime | 73 |
| Total | 100 |

All the ingredients used in this formulation are in a fine powder form. The percent benzalkonium chloride is only 2%, it is mixed with small portions of ferrous sulfate. The resultant mixture of benzalkonium chloride and ferrous sulfate is further mixed with half the quantity of lime followed by the remaining quantity of lime to complete the batch.

In another embodiment, a different process of manufacture can be used. In this, benzalkonium chloride is first dissolved in water, spread over lime and dried. The resultant powder is then mixed with ferrous sulfate. In another embodiment, the solution of benzalkonium chloride is spray-dried over a mixture of lime and ferrous sulfate.

EXPERIMENT V

In another example, green or brown color and a suitable fragrance such as, rose, lily, petunia, jasmine, lavender and marigold. Lime and ferrous sulfate are off-white in color and the powder spread is visible on the grass (Table VI). Addition of 1 to 2% green or brown color to the formulation helps it blend with the lawn. The role of fragrance is obvious. It makes the environment more appealing and produces nice fragrance in the backyard.

TABLE VI

| A representative complete Anti-moss formulation | |
|---|---|
| Ingredient | Percent, w/w |
| Ferrous sulfate | 25 |
| Benzalkonium chloride | 2 |
| ZVI | 15 |
| Jasmine flavor | 2 |
| Green color | 2 |
| Lime | 54 |

Apart from killing or controlling moss, the current formulation may have other applications. Ferrous sulfate is also useful to prevent depletion of phosphorous from pasture, turf-grass and filter strips. The current formulations can be mixed with manure to be spread over pasture, turf-grass and filter strips and it will prevent losses of phosphorous to the environment.

The proposed invention produced formulations to kill moss and the products are inexpensive, easy to use, easily available and non-toxic to plants, animals and human beings.

What is claimed is:

1. A combination of immediate release and sustained release powder to control moss and liverwort, comprising of a homogenous mixture of an immediate release portion comprising of a ferrous salt in 5 to 60% by weight, wherein the said immediate release portion is released at the beginning of application, and a sustained release portion comprising of zero valent iron in 1 to 60% by weight, wherein the said sustained release portion is released over 2 years period and lime as a carrier material in 20 to 80% by weight.

2. A combination of immediate release and sustained release powder to control moss and liverwort in claim 1 wherein the ferrous salt is selected from a group consisting of ferrous sulfate and ferrous ammonium sulfate and combinations thereof.

3. A combination of immediate release and sustained release powder to control moss and liverwort in claim 1 wherein the lime is selected from a group consisting of high calcium quicklime and dolomitic quicklime and combinations thereof.

4. A combination of immediate release and sustained release powder to control moss and liverwort in claim 1 further including a green or brown coloring agent in 0.1 to 5% by weight.

5. A combination of immediate release and sustained release powder to control moss and liverwort in claim 1 further including an antimicrobial agent in 0 to 10% by weight; selected from a group consisting of benzalkonium chloride, dichlorophen, and didecyldimethyl ammonium chloride and combinations thereof.

6. A combination of immediate release and sustained release powder to control moss and liverwort in claim 1 further including a fragrance in 0 to 10% by weight; selected from a group consisting of rose, lily, petunia, jasmine, lavender, gardenia, vanilla and marigold and combinations thereof.

* * * * *